United States Patent [19]

Giraud et al.

[11] Patent Number: 5,342,378

[45] Date of Patent: Aug. 30, 1994

[54] SECTIONING DEVICE FOR LAMELLAR SURGERY

[75] Inventors: Clarence E. Giraud, Mesa; Russell G. Koepnick, Phoenix, both of Ariz.

[73] Assignee: Micro Precision Instrument Company, Mesa, Ariz.

[21] Appl. No.: 110,323

[22] Filed: Aug. 20, 1993

Related U.S. Application Data

[63] Continuation of Ser. No. 775,178, Oct. 11, 1991, abandoned.

[51] Int. Cl.⁵ .............................................. A61F 9/00
[52] U.S. Cl. .................................. 606/166; 606/167; 606/169
[58] Field of Search ............... 606/166, 161, 169, 167

[56] References Cited

U.S. PATENT DOCUMENTS

| | | | |
|---|---|---|---|
| 4,180,075 | 12/1979 | Marinoff | 606/166 |
| 4,429,696 | 2/1984 | Hanna | 606/172 |
| 4,662,370 | 5/1987 | Hoffman et al. | 606/166 |
| 4,750,491 | 6/1988 | Kaufman et al. | 606/166 |
| 4,763,651 | 8/1988 | Kaufman et al. | 606/166 |
| 4,796,623 | 1/1989 | Krasner et al. | 606/166 |
| 4,807,623 | 2/1989 | Liebermann | 128/395 |
| 4,884,570 | 12/1989 | Krumeich et al. | 606/166 |
| 5,133,726 | 7/1992 | Ruiz et al. | 606/166 |

*Primary Examiner*—Edgar S. Burr
*Assistant Examiner*—John S. Hilten
*Attorney, Agent, or Firm*—Cahill, Sutton & Thomas

[57] ABSTRACT

A keratome is machined from a single block of material to form front and back portions that cannot become distorted during use. The blade is held at a reduced angle and a surface defining a chamber for receiving the slice intersects the blade at a tangent. The adjustable plate overlaps the blade a predetermined amount. The lower edge of the plate, adjacent the blade, is shaped for an improved cut, as is the blade itself. The suction ring is laser welded to avoid distortion of the channel for the keratome and an applanator is shaped to prevent relative motion of the applanator along the channel.

10 Claims, 2 Drawing Sheets

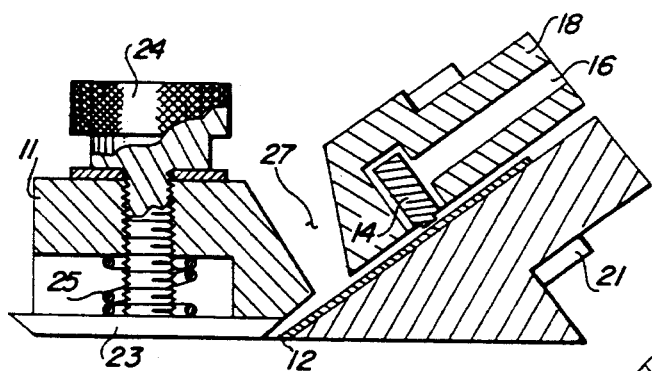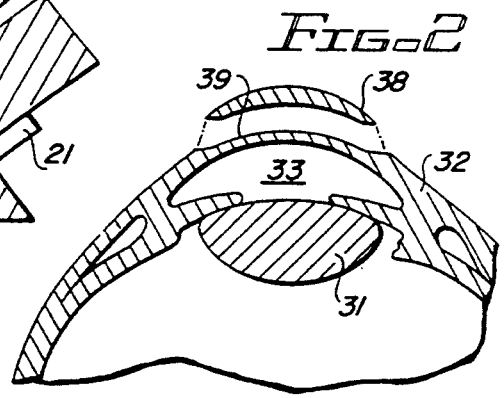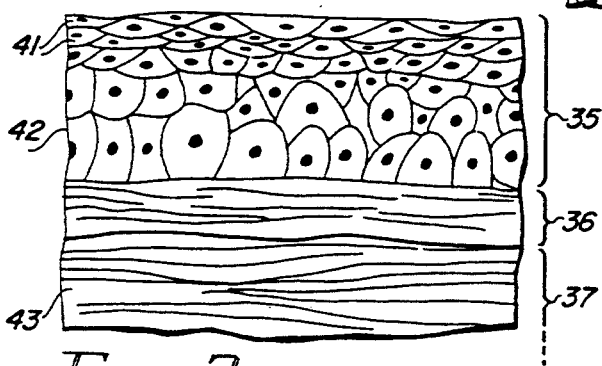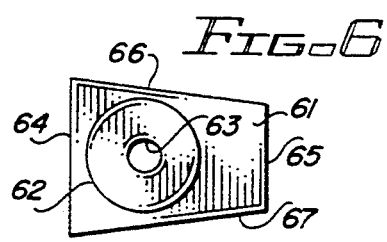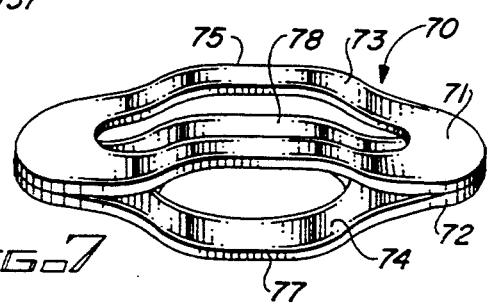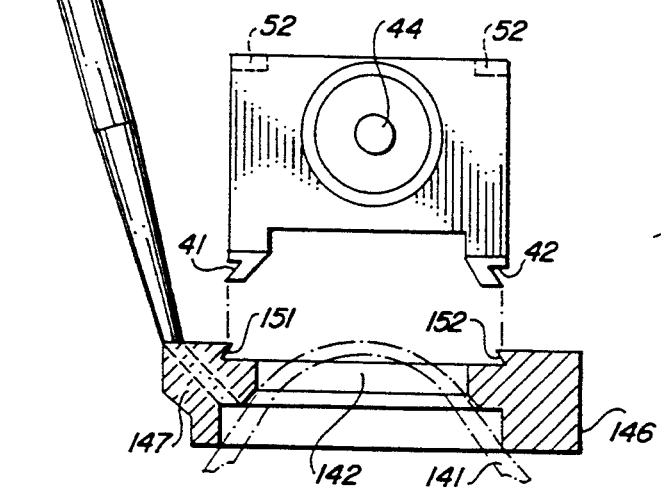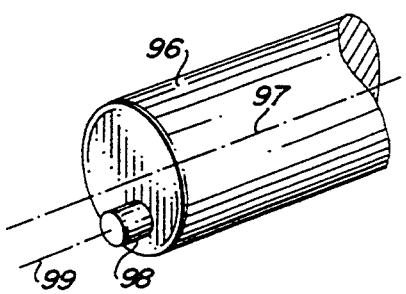

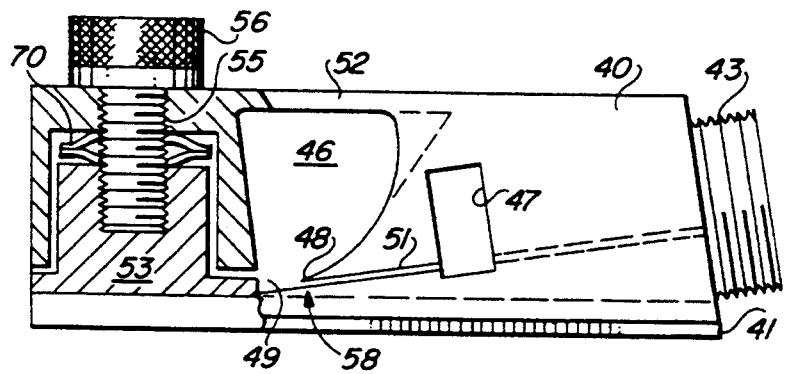
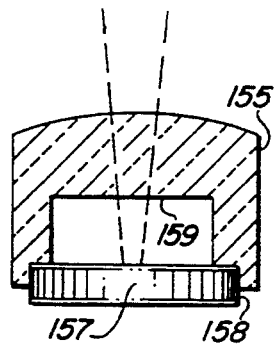
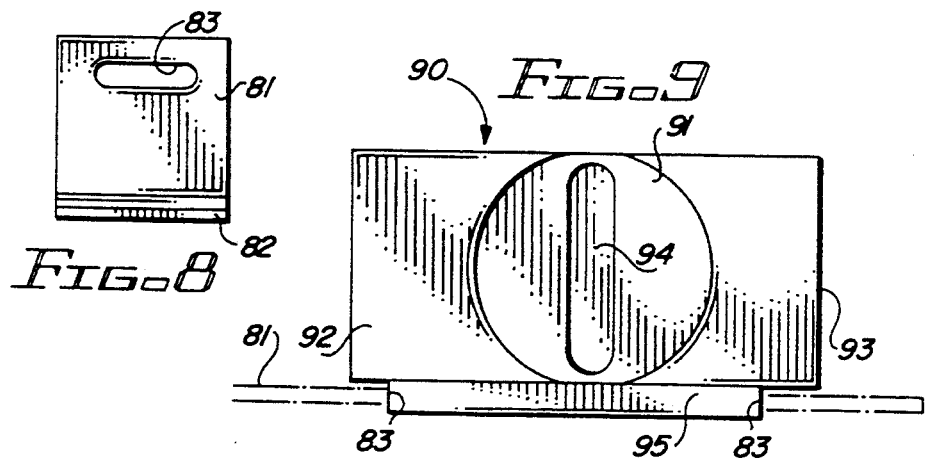
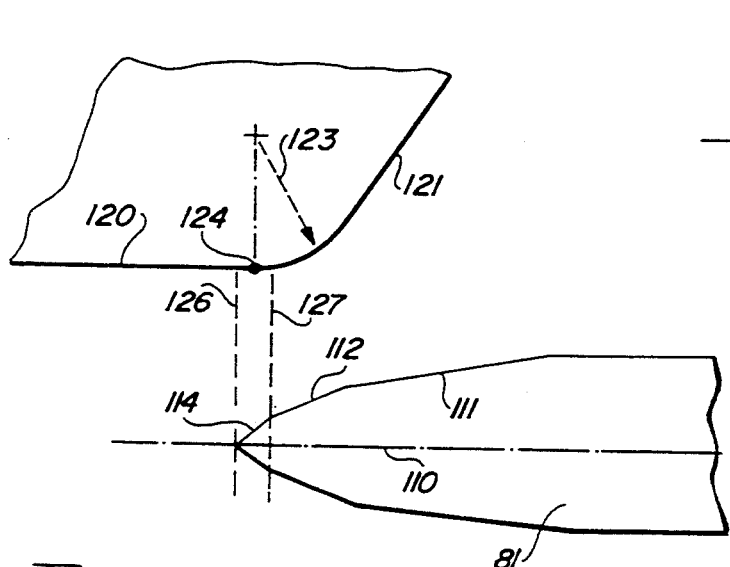
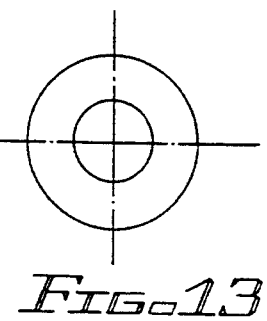

SECTIONING DEVICE FOR LAMELLAR SURGERY

This is a continuation of application Ser. No. 07/775,178 filed Oct. 11, 1991, abandoned.

BACKGROUND OF THE INVENTION

This invention relates to surgical apparatus for surgically removing thin sections of tissue and, in particular, to a keratome for use in ophthalmological procedures.

The eye is a compound optic comprising a cornea (the transparent, outer layer) and a lens. Approximately seventy percent of the focusing of light in the eye is performed by the cornea; viz. approximately forty-two diopters. (A diopter is a standard unit of measurement and is the reciprocal of the focal length of a lens in meters.) The remainder, about eighteen diopters, is performed by the lens of the eye. In the average total refraction of sixty diopters, a variation of less than five diopters is considered normal variation among a population. An error of more than five diopters is considered pathological.

Dr. Jose Barraquer of Bogota, Columbia, suggested in 1949 that many problems with vision could be corrected by surgically changing the shape of the cornea; viz. its curvature. Dr. Barraquer first published in 1964 the results of a procedure to correct myopia (nearsightedness). The procedure took a thin section from the front of the cornea, centered above the pupil. He froze the section, shaped it with a cryogenic lathe, thawed it, and re-attached it to the eye. The equipment for performing this procedure is large, expensive and not entirely satisfactory. In general, progress in this area has been limited by lack of suitable equipment; in particular, by a lack of equipment for removing smooth, round tissue of the desired thickness from a cornea and, at the same time, leaving a smooth bed for the tissue to adhere to when it is replaced.

The tool used for making corneal slices is known as a keratome. Some keratomes resemble a tiny block plane having an overall length of about three centimeters. Unlike a plane, the blade in the keratome oscillates from side to side at high speed to slice the tissue.

FIG. 1 illustrates a keratome of the prior art. The keratome comprises an elongated body 11 having a slanted surface at one end thereof for receiving blade 12. Cam 14 engages a hole in blade 12 to drive blade 12 from side to side (into and out of the plane of the drawing). Apparatus (not shown) extending through channel 16 in head 18 drives coupling member 14. Suitable drive means can be electrical or pneumatic. Head 18 is held in place by collar 21, which is threaded on to head 18 and a portion of body 11. Head 18 and body 11 together form a slot for containing blade 12. The front end of the keratome has a vertically adjustable plate 23. The difference in height between the edge of adjustable plate 23 and the edge of blade 12 determines the thickness of the section removed from the cornea. Adjustment means 24 provides a very small movement of plate 23, which is biased by spring 25 to avoid backlash.

(As used herein, terms implying direction are for convenience in referring to the drawings, e.g. "front," "back," "vertical," otherwise the terms are of no significance.)

In use, the plate is adjusted to an appropriate height. A tool known as an suction ring is applied to the front of the eye, centered over the iris. Suction rings are made in different thicknesses to vary the diameter of the section removed from the cornea. When placed over the eye, the suction ring locates, confines, and slightly bulges the cornea, by raising the interocular pressure, to flatten the cornea against the plate for slicing by the keratome. The suction ring has a dovetail fitting for receiving the lower edges of the keratome, which has a corresponding dovetail shape.

The power is applied to the keratome, which causes the blade to oscillate at ten to twenty thousand cycles per minute. The keratome is slid through the dovetail in the suction ring, causing a section of tissue of the cornea to be removed and pass into interior chamber 27 of the keratome. The surgeon then recovers the tissue from the keratome and later replaces it on the cornea.

FIG. 2 is a simplified illustration of a cross-section of a portion of a human eye. Eye 30 comprises lens 31 separated from cornea 32 by anterior space 33. In the central region above lens 31, cornea 32 has a thickness of about five hundred twenty microns which increases toward the conjunctiva (toward the sides).

The cornea itself actually comprises five layers, the outer three of which are illustrated in FIG. 3. The outermost layer is known as the epithelium layer, denoted as layer 35 in FIG. 3, and is fifty to ninety microns thick. The Bowman layer, denoted as layer 36, separates the epithelium from the substantia propria or stroma, layer 37. The Bowman layer is about twelve microns thick. Layer 37 comprises most of the thickness of the cornea, four hundred to four hundred and fifty microns.

During keratomileusis in-situ for myopia, two sections are removed from the cornea. A first section is cut as illustrated in FIG. 2, yielding disk 38. The disk is not flat because the cornea is flattened somewhat prior to the cut being made. After the cut, the disk returns to a three dimensional shape. Bed 39 is the outer surface of the remaining cornea. A second cut is made to remove a second disk. Disc 38 is then re-attached. (Disk 38 contains the critical Bowman layer). The effect is to flatten or reduce the curvature of the cornea, correcting nearsightedness.

The requirement for smooth cuts with no rough edges nor bed is compounded when two cuts are made. A smooth bed is especially difficult to leave after the second cut because of the structure of the cornea. Specifically, the epithelium or outer layer of the cornea comprises lamellar (thin, plate-like) cells 41 (FIG. 3) on its outer surface and columnar cells 42 on its inner surface. The columnar cells are more pliable and tend to yield rather than be cut by a blade. Also, with the somewhat tougher outer layer removed, the softer, fibrous tissue in layer 37 is more difficult to cut smoothly. Prior to the present invention, no keratome has been available which is capable of making perfectly round, smooth, second cuts for this procedure.

The risk of having rough edges and an irregular periphery restricts the range of thicknesses of the cuts that can be made and, hence, the range of corrections that can be obtained because the cuts must be relatively thick. This makes the procedure useful only for severely myopic patients; e.g. where the desired correction is eight diopters or more. It is highly desirable to be able to cut thin, precise disks, which will enable the surgeon to use the procedure for correction of low and mid-myopia (two to three diopters and four to eight diopters). Further, keratomes of the prior art leave undesirable microscopic ridges and valleys across the surface of the cornea, even in the hands of highly skilled surgeons.

Whether one disk or two disks are cut, a deficiency with keratomes of the prior art is the inconsistency of the cuts; i.e. a given combination of keratome setting and suction ring did not yield consistent, predictable results. Instead, the shapes and thicknesses of the disks varied and the remaining beds on corneas were rough. Since the correction is relative to the thickness of the cut and the smoothness of the bed, a different instrument is necessary.

In view of the foregoing, it is therefore an object of the invention to provide a surgical tool for obtaining accurate, smooth cuts of delicate tissue.

Another object of the invention is to provide an improved keratome for enabling one to make cuts having smooth edges and surfaces.

A further object of the invention is to provide an improved keratome capable of consistently cutting smooth, round disks of the diameter and thickness desired by the surgeon to correct a greater range of myopia.

Another object of the invention is to provide a keratome capable of making smooth, round, cuts on a human cornea.

A further object of the present invention is to provide a keratome that can produce consistent results from device to device.

SUMMARY OF INVENTION

The foregoing objects are achieved in the invention wherein the keratome holds the blade at a reduced angle and wherein braces reinforce the connection of the front and back portions of the keratome body so that the body is rigid throughout its length. The blade is sharpened to a particular bevel angle and honed at two different angles to produce a superior edge. The interior chamber of the keratome body is shaped for receiving the tissue being cut and the blade is covered with an extension for guiding the tissue through the keratome body. In addition, the blade is held within a slot machined to an extremely fine tolerance to eliminate vertical movement of the blade when it is cutting. The adjustable plate is trapezoidal to assure that it can be assembled to the body in only one way. The construction of the plate insures that it stays parallel with the cutting edge of the blade. The edge of the blade is oriented with respect to the adjacent edge of the adjustable plate to insure a clean cut. In addition, the adjustable plate is manufactured and mounted in a way which assures uniform application of pressure across its entire surface. In accordance with another aspect of the present invention, the suction rings are made by laser welding the stem to the ring and then forming the dovetail in the ring. In accordance with another aspect of the invention, the applanators have a diameter greater than the ring to overlap the ring on two sides, thereby precluding any movement of the applanator during use.

A more complete understanding of the present invention can be obtained by considering the following detailed description with the accompanying drawings in which:

FIG. 1 illustrates a keratome of the prior art.

FIG. 2 illustrates a cross-section of a portion of a human eye.

FIG. 3 illustrates a detail of the structure of a human cornea.

FIG. 4 illustrates a suction ring and an end view of a keratome in accordance with the invention.

FIG. 5 illustrates a side view of a keratome in accordance with the invention.

FIG. 6 illustrates the adjustable plate used in the keratome of the invention.

FIG. 7 illustrates a spring means for biasing the adjustable plate in accordance with the invention.

FIG. 8 illustrates a blade in accordance with the invention.

FIG. 9 illustrates a drive cam in accordance with the invention.

FIG. 10 illustrates the drive shaft for moving the cutting blade.

FIG. 11 illustrates a detail of the alignment of the blade with the adjustable plate in accordance with the invention.

FIG. 12 illustrates an applanator in accordance with the invention.

FIG. 13 illustrates the markings on the upper inner surface the applanator.

DETAILED DESCRIPTION

Referring to FIGS. 4 and 5, the main frame of keratome 40 is made from a single block of stainless steel having dovetails 41 and 42 formed in the lower edges thereof. Threaded connection 43 is at the rear of keratome 40 and has bore 44 cut therein. A drive shaft fits into bore 44. Connection 43 attaches keratome 40 to suitable drive apparatus, not shown and well known per se in the art, for example for dental drills and keratomes of the prior art.

Chambers 46 and 47 extend from side to side through keratome 40. Chamber 46 is partially defined by curved surface 48 which extends over substantially the whole length of the blade, except for an exposed portion in region 49. The blade is located in slot 51 which extends from side to side and connects chambers 46 and 47. Chamber 47 receives the drive cam which moves the blade from side to side. Bore 44 connects with chamber 47.

Chamber 46 does not extend to the top of keratome 40, forming braces 52 on each side of the top which interconnect the front and rear portions of keratome 40, greatly stiffening it to prevent any distortion of the original configuration, which would adversely affect the precision of the cut. Braces 52, as illustrated in FIG. 4, allows access to chamber 46 through the top of keratome 40. Alternatively, braces 52 could be a surface extending from side to side, enclosing the top of chamber 46.

The front portion of keratome 40 defines chamber 53 for receiving the adjustable plate and bias spring, as described in conjunction with FIGS. 6 and 7. Bore 55 passes through the upper surface of chamber 53 and receives column 62 (FIG. 6). Knob 56 contains a screw with extends through bore 55 to engage threaded bore 63.

In one embodiment of the invention, the length of keratome 40, not including connector 43, was 1.350 inches. The radius of curvature of surface 48 was 0.225 inches. The radius is not critical although it is preferably large with respect to the dimensions of chamber 46. What is important is that the blade be tangential or nearly tangential to surface 48 at their intersection, point 58. This relationship, curved surface 48, and the volume of chamber 46 assure that the corneal disk will not fold or bind and is easily removed from the keratome by the surgeon.

Chamber 47 is preferably machined to dimensions equal to the dimensions of the cam, plus 0.0005 inch. This precludes unwanted movement of the cam and assures steady driving of the blade. Similarly, slot 51 is preferably machined to the thickness of the blade, plus 0.0005 inch. This prevents the blade from fluttering as it oscillates, as seen in keratomes of the prior art. Since keratome 40 is machined from a single block of steel, the height of slot 51 can be precisely controlled, in contrast to the two piece assembly of the prior art.

Slot 51 is angled with respect to the bottom of the keratome. In the prior art, this angle was twenty-six degrees or more. In the present invention, it has been found that a blade angle of less than fifteen degrees is required. A preferred embodiment of the present invention uses an angle of nine degrees relative to the bottom of the keratome. It is believed that this causes the blade to slice rather than scrape the cornea.

FIG. 6 is a top view of an adjustable plate constructed in accordance with the invention. Plate 61 is attached to column 62 having threaded bore 63 therein. Plate 61 preferably has a trapezoidal shape to permit assembly in only one direction. Chamber 53 also has a corresponding trapezoidal cross-section in a plane parallel to the bottom of keratome 40. Edges 64 and 65 are parallel. Edges 66 and 67 are not parallel but draw closer to one another toward edge 65. The amount of taper is a matter of design. A taper of 0.04 inch per inch has been found suitable. Edge 65 is located adjacent the blade. Column 62 is of sufficient diameter, e.g. 0.18 inches, to assure that plate 61 can be calibrated to the desired position and not change during use. Bore 63 preferably has a fine thread to allow small adjustments to be made in the space between the plate and the blade, because that space primarily determines the thickness of the cut. Sixty threads per inch has been found suitable.

The adjustable plate is preferably made from a single piece of stainless steel. This assures stability between the bolt and the plate itself. The bottom surface of plate 61 is ground flat to within 0.0005 inches and then lapped. The flatness assures an accurate cut and the lapping assures that the cornea will not be scratched or otherwise damaged by the tool. In addition, the lower portion of edge 65 is beveled and has a radius, as further described in connection with FIG. 11.

FIG. 7 illustrates spring means used to bias the adjustable plate. Specifically, spring means 70 comprises resilient, annular disks 71 and 72 having oppositely curved portions 73 and 74. In addition, a part of the perimeter of each disk is flattened to assure that the disks cannot rotate relative to one another during use. Flats 75, 76, 77 and 78 are parallel to the inner side walls of chamber 53 and are slightly spaced therefrom. The upper surface of disk 71 rests on the inside of the upper surface of chamber 53. The lower surface of disk 72 rests on the upper surface of adjustable plate 61. Bolt 62 fits within the opening in the center of disks 71 and 72. While only two disks are shown, more disks can be used. In addition, depending upon the height of chamber 53, flat annular disks can be added between the curved resilient disks. It is preferred that the range of movement of plate 61 be limited so that the maximum depth of cut does not exceed the thickness of the average cornea, five hundred and twenty microns.

FIG. 8 illustrates a blade constructed in accordance with the invention. The blade comprises surgical steel cut to the width of keratome 40. Edge 82 is sharpened as described in conjunction with FIG. 11. Opposite edge 82 is keyway 83 for receiving a key from the drive cam illustrated in FIG. 9. Blade 81 typically has a thickness of 0.009 in.

Cam 90 is a rectangular block having the same width as the keratome. Recess 91 is formed in a broad face, forming shoulders 92 and 93. Slot 94 is formed in recess 91. Key 95 is formed on the bottom surface of cam 90 and has a shape corresponding to keyway 83, into which it fits. It is preferred that the recess and slot not extend into the bottom surface adjacent key 95 to assure a full bearing surface for the cam.

In use, key 95 is inserted into keyway 83 in blade 81 and the two together slid sideways into the keratome block illustrated in FIG. 5. The slotted major face of cam 90 must face connector 43 to accept the drive shaft.

FIG. 10 illustrates a portion of the drive mechanism, specifically the drive shaft and pin. The mechanism for turning the driveshaft is well known per se in the art. Drive shaft 96 ends in a flat face having pin 98 eccentrically mounted thereon. The distance between the axis 97 of shaft 96 and axis 99 of pin 98 is the stroke of the blade. The stroke is a matter of design, but is typically 0.150 in. The end of shaft 96 fits within recess 91 of cam 90. Pin 98 fits into slot 94. As drive shaft 96 rotates, the rotational motion is converted into reciprocal motion by cam 90, which drives blade 81 from side to side in keratome 40. It is preferred that the shaft be spring loaded to provide some compliance along its length while it is driving cam 90.

Because of the recess forming shoulders 92 and 93, and the fact that the recess does not extend through to the key, one obtains a safety advantage if the pin should break off from drive shaft 96 in that the cam and blade would be trapped within their chambers by the drive shaft which fits in recess 91.

FIG. 11 illustrates the relationship between the cutting edge of the blade and the corner of adjustable plate 61. The blade is preferably symmetrical about axis 110. The edge of blade 81 is formed by grinding at an angle of six degrees relative to axis 110 in region 111. This is followed by honing at an angle of eight degrees in region 112, which is followed by honing at an angle of eleven degrees in tip 114. This edge treatment has been found to produce a superior cutting edge for cutting a cornea.

FIG. 11 also illustrates the edge treatment of the underside of edge 65, which is positioned adjacent blade 81. Edge 65 preferably has a bevel 121 of twenty-seven degrees, plus or minus one degree, relative to lower surface 120. The bevel need not extend the full thickness of plate 61. In a preferred embodiment of the present invention, it occupies only the lower half of edge 65. The extent of the bevel is a matter of design. Its purpose is to provide clearance and guidance for the corneal disk coming off the blade. The bevel and the lower surface of adjustable plate 61 should not meet at a corner or edge. Thus, the surfaces are connected by radius 123. The specific value of the radius is a matter of design, but the radius must be there to protect the outer surface of the cornea. Lower surface 120 is tangent to the radius at their intersection, a line perpendicular to the plane of the drawing, represented by point 124.

In Dr. Barraquer's work, the keratome did not have a adjustable plate, but a set of interchangeable, fixed plates of different thicknesses. While the plate overlapped the blade, the location of the edge of the plate relative to the edge of the blade was not precise. In keratomes of the prior art having adjustable plates, such as illustrated in FIG. 1, the blade and the plate do not overlap: the plate can be removed with the blade in place. In short, it has not been recognized that the location of the edge of the blade relative to the edge of the plate is important.

It has been found that the effectiveness of the cut depends, in part, upon the locations of the edge of blade 81 and the corner of plate 61. Specifically, optimum results are obtained if point 124 is located above tip 114 of blade 81; i.e. between lines 126 and 127. It is believed that locating point 124 above tip 114 provides support for the cornea during and immediately after cutting the cornea, thereby improving the smoothness of the cut, particularly at the end of the cut, which has heretofore been a problem area. Because some overlap is good does not mean that more overlap is better. It has also been found that greater overlap produces inferior cuts, compared to that obtained with the plate properly located horizontally.

Referring to FIG. 4, suction ring 140 is placed over cornea 141. Circular opening 142 is located over the center of the front of the eye. Suction is provided through handle 145, which is hollow and has fitting 146 at the end thereof for connection to a vacuum system. Bore 147 connects handle 145 with the interior of ring 140. The reduced pressure draws cornea 141 up into aperture 142, which typically has a diameter of 11.25 mm. Dovetails 41 and 42 of keratome 40 fit into corresponding dovetails 151 and 152 in suction ring 140. The front of the keratome is inserted into the channel and the keratome (with the blade oscillating) slides across ring 140, cutting a disk from the cornea. The thickness of the disk is regulated by the setting of adjustable plate 61 before the operation.

In the prior art, the ring was machined and the handle attached, either by welding or by screwing the threaded end of the handle into a threaded bore in the ring. The screw fitting was not a reliable connection, weak and prone to leakage. Welding the handle distorted the geometry of the ring so that the dovetail joints did not function smoothly. In accordance with another aspect of the invention, the ring is machined, except for the dovetails. The handle is attached by laser welding, which heats the body of the ring very little, and then the dovetails are formed. The result is a precise, smooth joint between the keratome and the ring.

The diameter and thickness of the disk removed from the cornea depends upon the thickness of the suction ring and the depth of cut as determined by the setting of adjustable plate 61. Choosing the right suction ring is done with what is known as an applanator; a transparent, acrylic cylinder having a domed or spherical top to give some enlargement of the viewing area. FIG. 12 illustrates an improved applanator in accordance with another aspect of the invention. Applanator 155 is of greater diameter than ring 157 and has shoulder 158 formed therein for engaging the outside of ring 157 at each end of the channel. The sidewall extends down between the dovetails in ring 157, not shown in FIG. 12. Thus, applanator 155 cannot move relative to ring 157, thereby giving a consistent view of the cornea. Flats are formed in the sides of the applanator, as in the prior art, with grooves for clearing the handle. In accordance with the invention, the grooves are dimensioned to fit closely around the handle, thereby further stabilizing the measurement and assuring that the applanator and ring are located accurately.

FIG. 13 illustrates the indicia marked on interior surface 159 of applanator 155. The inner circle has a diameter equal to that marked on the applanator (3.5–6.5 mm.) and aids in centering the applanator. The outer circle has a diameter of 7.25 mm., which is the standard diameter of the first disk cut. The crosshairs aid in centering the ring and, in particular, aid in re-centering the ring for the second cut. Induced astigmatism can occur from several causes, one of which is that the ring was not centered for the second cut. (The second cut removes a smaller diameter disk so the first ring must be removed and a thinner ring used for the second cut.)

The keratome is preferably machined from a single block of 400 series stainless steel by what is known per se in the art as EDM (electron discharge machining). In order to assure the stability of the steel, it is heat treated (annealed) prior to cutting. The various channels, bores, and slots can then be cut in a reproducible manner, in part due to the stability of the material and in part due to the precision of EDM.

There is thus provided by the invention an improved keratome capable of making precise cuts wherein each cut has smooth edges and is free of ridges or valleys. Because of the smoothness of the cut, corrections of low and mid-myopia are achievable.

Having thus described the invention, it will be apparent to those of skill in the art that many modifications can be made within the invention. For example, while described in conjunction with a particular procedure, the use of the invention is not so limited. The invention can be used wherever smooth cuts of delicate tissue are desired. Although a dovetail connection between the keratome and the suction ring has been shown and described, it is understood that other connections providing the same function can be used, e.g. a bead and cove. While described as a threaded column on the adjustable plate receiving a threaded connector from the top of the keratome, it is understood that the reverse is equally effective: a threaded bolt attached to the plate fitting within a threaded column from the top of the keratome.

What is claimed is:

1. A keratome for making single or consecutive lamellar slices of human tissue, particular in the cornea of a human eye, said keratome comprising:

an elongated, unitary body having a front portion and a rear portion defining a chamber therebetween for receiving said slices, said chamber including a curved surface;

an adjustable plate in said front portion, said adjustable plate having a planar surface facing outwardly from said body;

means connected to said front portion for moving said adjustable plate in a direction perpendicular to said planar surface to adjust the thickness of a slice;

a slot extending from side to side through said rear portion, wherein said slot defines a plane at an angle of less than fifteen degrees and greater than zero degrees relative to said planar surface;

a blade in said slot, said blade
 (a) being movable from side to side in said slot,
 (b) having a cutting edge extending from said body past said planar surface, and
 (c) being approximately tangential to said curved surface.

2. The keratome as set forth in claim 1 wherein the plane of said slot is at an angle of nine degrees relative to said planar surface.

3. The keratome as set forth in claim 1 wherein said adjustable plate terminates in an edge adjacent said blade and is displaced from said cutting edge in said direction.

4. The keratome as set forth in claim 3 wherein said edge is beveled to form a beveled portion.

5. The keratome as set forth in claim 4 wherein said beveled portion is at an angle of twenty-seven degrees relative to said planar surface.

6. The keratome as set forth in claim 4 wherein the beveled portion and said planar surface are joined by a curved portion.

7. The keratome as set forth in claim 6 wherein the said planar surface intersects said curved portion along a tangent.

8. The keratome as set forth in claim 7 wherein said planar surface and said curved portion intersect along a line located above said cutting edge.

9. The keratome as set forth in claim 1 and further including a brace, interconnecting said front portion and said rear portion along the top of said chamber, for stiffening said keratome.

10. The keratome as set forth in claim 9 wherein a pair of braces interconnect said front portion and said rear portion along the top of said chamber.

* * * * *